United States Patent
Kang

(10) Patent No.: US 11,610,506 B2
(45) Date of Patent: Mar. 21, 2023

(54) METHOD AND APPARATUS FOR PROVIDING GUIDE INFORMATION ASSOCIATED WITH EXERCISE INTENSITY ON BASIS OF USER ACTIVITY INFORMATION

(71) Applicant: Samsung Electronics Co., Ltd., Gyeonggi-do (KR)

(72) Inventor: Seung Seok Kang, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 480 days.

(21) Appl. No.: 16/640,450

(22) PCT Filed: Aug. 21, 2018

(86) PCT No.: PCT/KR2018/009557
§ 371 (c)(1),
(2) Date: Feb. 20, 2020

(87) PCT Pub. No.: WO2019/039819
PCT Pub. Date: Feb. 28, 2019

(65) Prior Publication Data
US 2020/0211410 A1 Jul. 2, 2020

(30) Foreign Application Priority Data
Aug. 22, 2017 (KR) .................. 10-2017-0106273

(51) Int. Cl.
*G09B 19/00* (2006.01)
*G16H 20/30* (2018.01)
(Continued)

(52) U.S. Cl.
CPC ........ *G09B 19/003* (2013.01); *A63B 24/0075* (2013.01); *G16H 20/30* (2018.01);
(Continued)

(58) Field of Classification Search
CPC ...... G09B 19/003; G16H 20/30; G16H 40/67; A63B 24/0075; A63B 2024/0068; A63B 2225/20; A61B 5/1118
(Continued)

(56) References Cited

U.S. PATENT DOCUMENTS

2009/0069156 A1  3/2009  Kurunmaki et al.
2013/0268292 A1  10/2013  Kim et al.
(Continued)

FOREIGN PATENT DOCUMENTS

KR  10-2006-0007236 A  1/2006
KR  10-2014-0015678 A  2/2014
(Continued)

OTHER PUBLICATIONS

Korean Search Report dated Sep. 8, 2021.
(Continued)

*Primary Examiner* — Jay Trent Liddle
*Assistant Examiner* — Alyssa N Brandley
(74) *Attorney, Agent, or Firm* — Cha & Reiter, LLC

(57) ABSTRACT

Various embodiments of the present disclosure provide a method and an apparatus for providing personal coach for user's exercise in an electronic device. According to various embodiments of the present disclosure, an electronic device may include sensor circuitry and a processor, wherein the processor may be configured to determine at least one activity information which satisfies a designated condition among one or more activity information previously obtained in relation to a user motion, to determine a first exercise intensity for the user, based at least on variation of the at least one activity information over time, to determine a second exercise intensity by adjusting the first exercise intensity, based at least on a previous target of exercise of the (Continued)

user, and to provide guide information associated with the second exercise intensity. Various embodiments are feasible.

15 Claims, 19 Drawing Sheets

(51) Int. Cl.
  *G16H 40/67* (2018.01)
  *A63B 24/00* (2006.01)
  *A61B 5/11* (2006.01)

(52) U.S. Cl.
  CPC ............ *G16H 40/67* (2018.01); *A61B 5/1118* (2013.01); *A63B 2024/0068* (2013.01); *A63B 2225/20* (2013.01)

(58) Field of Classification Search
  USPC .......................................................... 434/247
  See application file for complete search history.

(56) References Cited

U.S. PATENT DOCUMENTS

2016/0213979 A1    7/2016  Lee et al.
2016/0354636 A1*  12/2016  Jang ........................ A61B 5/681
2018/0345081 A1   12/2018  Lee et al.

FOREIGN PATENT DOCUMENTS

| KR | 10-2016-0054325 A | 5/2016 |
| KR | 10-2016-0091694 A | 8/2016 |
| KR | 10-1715369 B1 | 3/2017 |
| KR | 10-2017-0050190 A | 5/2017 |

OTHER PUBLICATIONS

"David F. Cameron Model"; Time-equivalence Model; 3 pages http://www.cs.uml.edu/~phoffman/cammod.html.

J.G. Purdy; "More information on Purdy points"; 3 paes http://www.cs.uml.edu/~phoffman/xcinfo3.html.

"Explaining the Performance Predictors"; Run-Down.com; 1 page.

James D. George et al.; "VO2max estimation from a submaximal 1-mile track jog for fit college-age individuals" pp. 401-406.

\* cited by examiner (a)

(b)

METHOD AND APPARATUS FOR PROVIDING GUIDE INFORMATION ASSOCIATED WITH EXERCISE INTENSITY ON BASIS OF USER ACTIVITY INFORMATION

CROSS REFERENCE TO RELATED APPLICATIONS

This application is a National Phase Entry of PCT International Application No. PCT/KR2018/009557, which was filed on Aug. 21, 2018, and claims a priority to Korean Patent Application No. 10-2017-0106273, which was filed on Aug. 22, 2017, the contents of which are incorporated herein by reference.

TECHNICAL FIELD

The present disclosure relates to a method and an apparatus for providing personal coach for user's exercise in an electronic device.

BACKGROUND ART

With advances of digital technology, various electronic devices such as a mobile communication terminal, a smart phone, a tablet personal computer (PC), a notebook, a personal digital assistant (PDA), a wearable device, a digital camera, or a personal computer are widely used.

Using the electronic device, various services (or functions) are provided for user's health care. For example, the electronic device may provide various exercise programs for the user's health care. A user may select any one of the various exercise programs of the electronic device, and effectively do the exercise according to a guide (or exercise coach) of the selected exercise program.

DISCLOSURE OF INVENTION

Technical Problem

Exercise programs provided from an electronic device do not consider a user's health condition or an exercise status, and are limited (or restricted) to exercise programs which are pre-installed in the electronic device or downloaded from outside. Accordingly, in the exercise program, a user may use only exercise coach based on an exercise amount (e.g., a running time, an exercise distance, etc.) of a repetitive pattern, regardless of the condition such as user health or exercise status. In addition, the user may personally create and use an exercise program, but the user needs to configure the exercise program on each occasion by considering his/her condition.

Various embodiments provide a method and an apparatus for providing a health care service using personal coach in consideration of a user's condition in an electronic device.

Various embodiments provide a method and an apparatus for providing guide information of an exercise intensity based on user activity information in an electronic device.

Various embodiments provide a method and an apparatus for generating a target of exercise for user's adequate exercise coach at a current timing in an electronic device.

Solution to Problem

According to various embodiments of the present disclosure, an electronic device may include sensor circuitry and a processor, wherein the processor may be configured to determine at least one activity information which satisfies a designated condition among one or more activity information previously obtained in relation to a user motion, to determine a first exercise intensity for the user, based at least on variation of the at least one activity information over time, to determine a second exercise intensity by adjusting the first exercise intensity, based at least on a previous target of exercise of the user, and to provide guide information associated with the second exercise intensity.

According to various embodiments of the present disclosure, a method for operating an electronic device may include determining at least one activity information which satisfies a designated condition among one or more activity information previously obtained in relation to a user motion, determining a first exercise intensity for the user, based at least on variation of the at least one activity information over time, determining a second exercise intensity by adjusting the first exercise intensity based at least on a previous target of exercise of the user, and providing guide information associated with the second exercise intensity.

According to various embodiments of the present disclosure, a recording medium may include a computer-readable recording medium which records a program for determining at least one activity information which satisfies a designated condition among one or more activity information previously obtained in relation to a user motion, determining a first exercise intensity for the user, based at least on variation of the at least one activity information over time, determining a second exercise intensity by adjusting the first exercise intensity based at least on a previous target of exercise of the user, and providing guide information associated with the second exercise intensity.

Advantageous Effects of Invention

An electronic device and its operating method according to various embodiments may provide a personalized health care service by considering the user's condition. According to various embodiments, the electronic device may provide the exercise coach for the user's exercise by setting a more adequate target of exercise at a current timing in consideration of the user's health or the exercise status. According to various embodiments, the most adequate target of exercise when the user starts the exercise may be adaptively set (generated) and provided, and the target of exercise based on the user selection may be registered as an exercise program. The electronic device according to various embodiments may contribute to its usability, convenience, or availability.

BEST MODE FOR CARRYING OUT THE INVENTION

Figure 1:
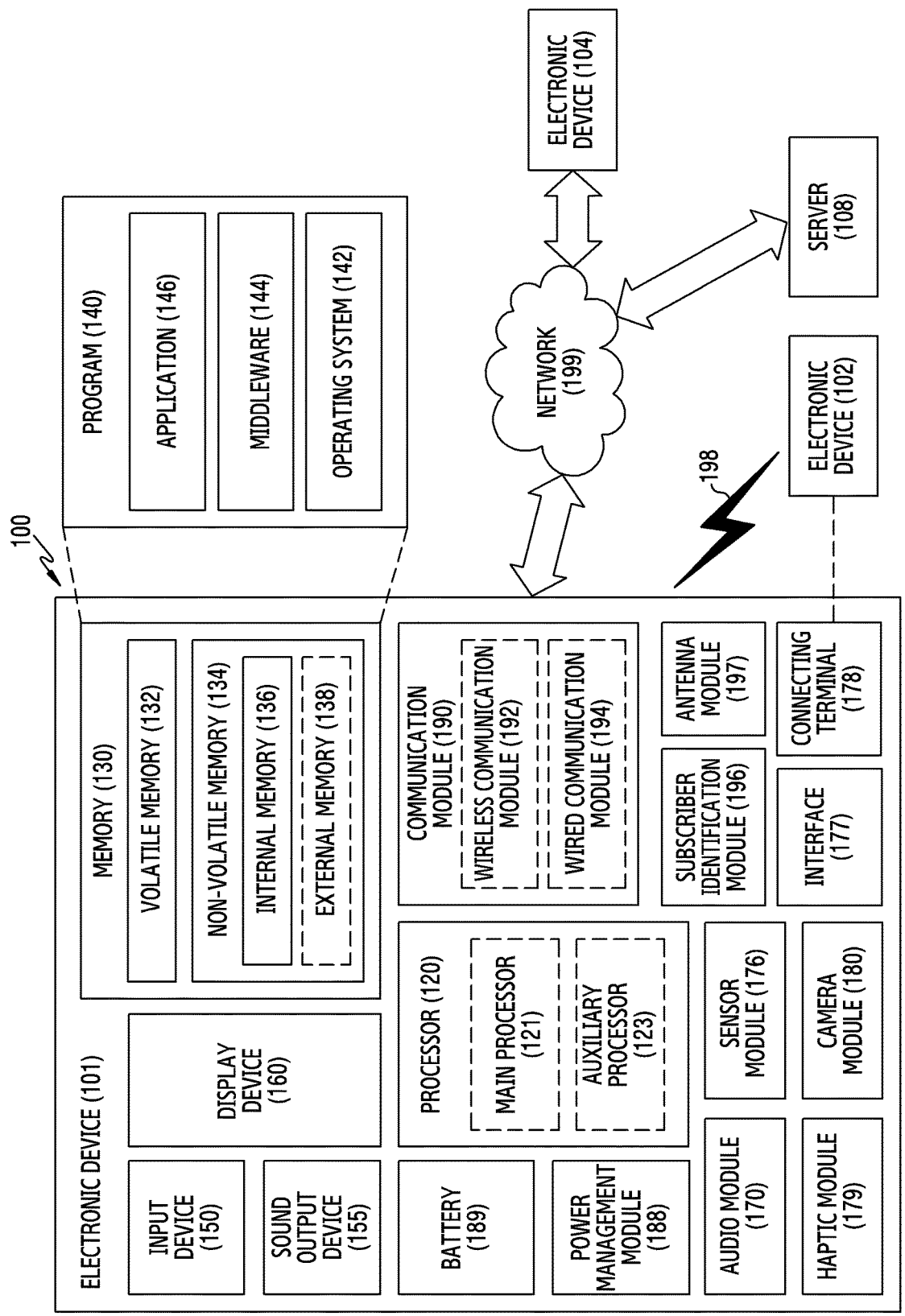
FIG. 1 is a block diagram of an electronic device in a network environment according to various embodiments.

Embodiments of the disclosure will be described herein below with reference to the accompanying drawings. However, the embodiments of the disclosure are not limited to the specific embodiments and should be construed as including all modifications, changes, equivalent devices and methods, and/or alternative embodiments of the present disclosure. In the description of the drawings, similar reference numerals are used for similar elements. While the present disclosure has been shown and described with reference to various embodiments thereof, it will be understood by those skilled in the art that various changes in form and details may be made therein without departing from the spirit and scope of the present disclosure as defined by the appended claims and their equivalents.

FIG. 1 is a block diagram illustrating an electronic device 101 in a network environment 100 according to various embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, or a keyboard.

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector), The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other.

The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include one or more antennas, and, therefrom, at least one antenna appropriate for a communication scheme used in the communication network, such as the first network 198 or the second network 199, may be selected, for example, by the communication module 190 (e.g., the wireless communication module 192). The signal or the power may then be transmitted or received between the communication module 190 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101.

According to an embodiment, all or some of operations to be executed at the electronic device 101 may be executed at one or more of the external electronic devices 102, 104. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
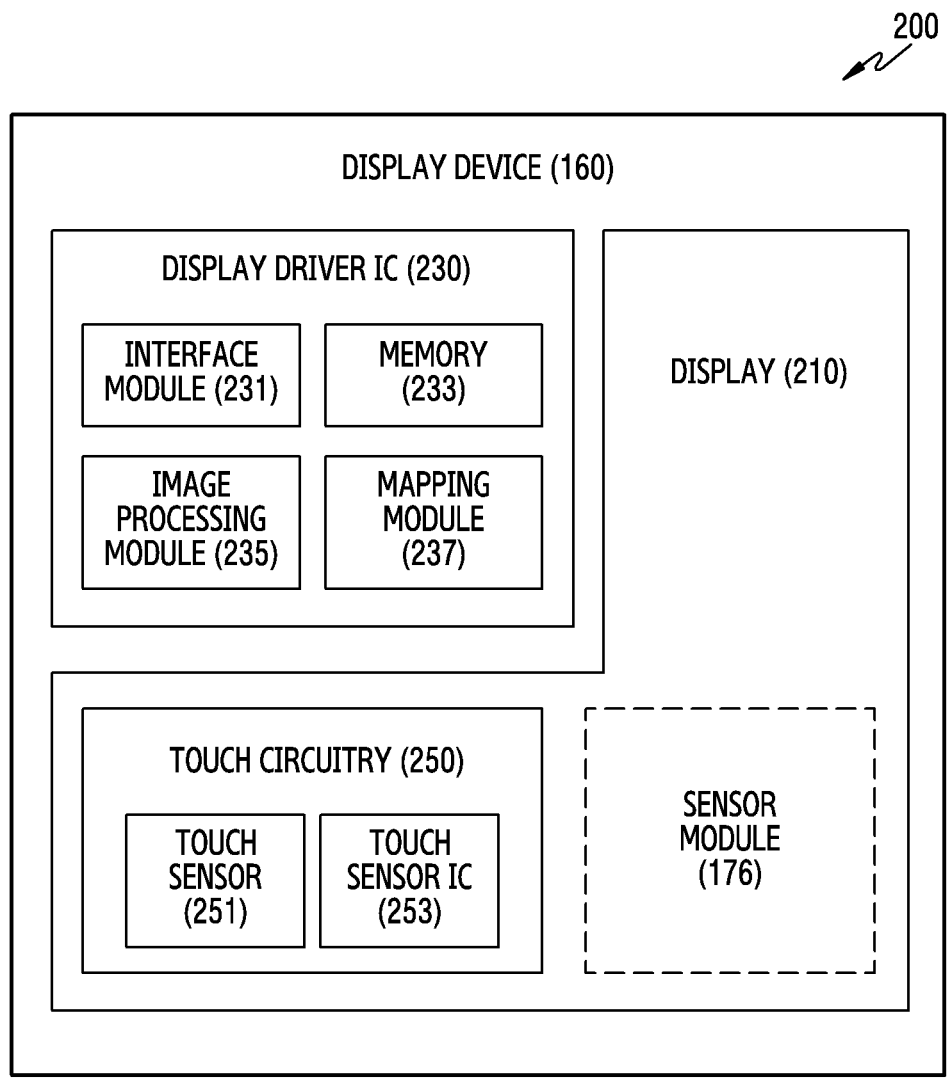
FIG. 2 is a block diagram of a display device according to various embodiments.

FIG. 2 is a block diagram 200 of a display device 160 according to various embodiments.

Referring to FIG. 2, the display device 160 may include a display 210 and a display driver integrated circuit (DDI) 230 for controlling the display 210. The DDI 230 may include an interface module 231, a memory 233 (e.g., a buffer memory), an image processing module 235, or a mapping module 237.

The DDI 230 may receive image information which contains image data or an image control signal corresponding to a command to control the image data, from the processor 120 (e.g., the main processor 121 (e.g., an application processor) or the auxiliary processor 123 operating independently from the function of the main processor 121), via the interface module 231. The DDI 230 may communicate with touch circuitry 250 or the sensor module 176 via the interface module 231. The DDI 230 may also store at least part of the received image information in the memory 233, for example, on a frame by frame basis.

The image processing module 235 may pre-process or post-process (e.g., adjust resolution, brightness, or size) at least part of the image data, based at least on characteristics of the image data or characteristics of the display 210.

The mapping module 237 may convert the image data pre-processed or post-processed by the image processing module 235, to a voltage value or a current value for driving pixels, based at least in part on attributes of the pixels (e.g., an array (a RGB stripe or a pentile structure) of the pixels, or the size of each subpixel) of the display 210. At least some pixels of the display 210 may be driven, for example, based on the voltage value or the current value, and thus the display 210 may display visual information (e.g., a text, an image, or an icon) corresponding to the image data.

According to an embodiment, the display device 160 may further include the touch circuitry 250. The touch circuitry 250 may include a touch sensor 251 and a touch sensor IC 253 for controlling the touch sensor 251. The touch sensor IC 253 may control the touch sensor 251 to detect a touch input or a hovering input at a particular position on the display 210 by measuring a change in a signal (e.g., a voltage, a quantity of light, a resistance, or a quantity of electric charges) corresponding to the particular position on the display 210, and provide the processor 120 with information (e.g., a position, an area, a pressure, or a time) of the detected touch input or hovering input. According to an embodiment, at least part (e.g., the touch sensor IC 253) of the touch circuitry 250 may be formed as part of the display 210 or the DDI 230, or as part of another component (e.g., the auxiliary processor 123) disposed outside the display device 160.

According to an embodiment, the display device 160 may further include at least one sensor (e.g., a fingerprint sensor, an iris sensor, a pressure sensor, or an illuminance sensor) of the sensor module 176, or a control circuit for the at least one sensor. In such a case, the at least one sensor or the control circuit for the at least one sensor may be embedded in one portion (e.g., the display 210 or the DDI 230) of the display device 160 or in one portion of the touch circuitry 250.

For example, if the sensor module 176 embedded in the display device 160 includes a biometric sensor (e.g., a fingerprint sensor), the biometric sensor may acquire biometric information (e.g., a fingerprint image) associated with a touch input received via a portion of the display 210. As another example, if the sensor module 176 embedded in the display device 160 includes a pressure sensor, the pressure sensor may acquire pressure information of a touch input received via a partial or whole area of the display 210. According to an embodiment, the touch sensor 251 or the sensor module 176 may be disposed between pixels in a pixel layer of the display 210, or over or under the pixel layer.

The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 3:
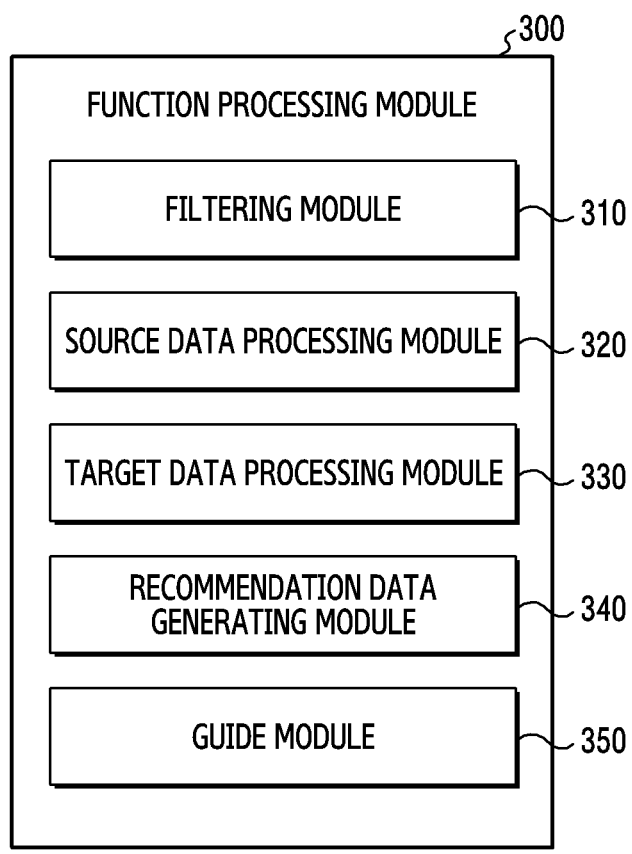
FIG. 3 is a diagram of an example of a function processing module in an electronic device according to various embodiments of the present disclosure.

FIG. 3 is a diagram of an example of a function processing module in an electronic device according to various embodiments of the present disclosure.

As shown in FIG. 3, FIG. 3 depicts an example of a function processing module 300 (or an exercise coach module) for providing a health care service in an electronic device (e.g., the electronic device 101 of FIG. 1) according to various embodiments. In various embodiments, the function processing module 300 may be included as a hardware module or a software module in a processor (e.g., the processor 120 of FIG. 1) including processing circuitry.

Referring to FIG. 3, the function processing module 300 may set and recommend an adequate target of exercise (e.g., an exercise amount based on an exercise distance and/or duration) at a current timing (e.g., today) of a user. In various embodiments, the function processing module 300 may include one or more modules for setting adequate target data for the user's current timing (e.g., today) and providing exercise coach based on the set target data. The function processing module 300 may include a filtering module 310, a source data processing module 320, a target data processing module 330, a recommendation data generating module 340, a guide module 350, and so on.

The filtering module 310 may process to filter exercise data. According to an embodiment, the filtering module 310 may filter at least one exercise data stored, based on at least one preset condition. In various embodiments, at least one condition may include a duration (e.g., a weekly, monthly, or yearly basis based on today) of the exercise data to extract, at least one criteria condition (e.g., over a specific distance or over a specific duration) of the exercise data, and the like.

The source data processing module 320 may normalize the exercise data filtered by the filtering module 310. The source data processing module 320 may, for example, smooth the filtered exercise data using exponential smoothing. According to an embodiment, the source data processing module 320 may obtain at least one source data (e.g., first source data or second source data) as the smoothing result. According to an embodiment, the source data may include at least one of distance data or duration data. In various embodiments, the first source data may indicate any one of the distance data or the duration data, and the second source data may indicate the other data (e.g., duration data) than the first source data (e.g., distance data).

The target data processing module 330 may target and predict the target data. According to an embodiment, the target data processing module 330 may determine at least one target data, based on at least one of the first source data, the second source data, user profile information, or user biometric information.

According to an embodiment, the target data processing module 330 may determine first target data (e.g., a target distance or a target duration) using the source data obtained using the smoothing. According to an embodiment, the target data processing module 330 may determine a type of the first target data, based on either the distance or the duration, which is preset, or user preference. According to an embodiment, if the set data is the distance, the target data processing module 330 may calculate a target distance as the first target data based on the source data. According to an embodiment, if the set data is the duration, the target data processing module 330 may calculate a target duration as the first target data based on the source data. According to an embodiment, the target data processing module 330 may analyze user preference (or tendency) based on user profile, and calculate the target distance or the target duration as the first target data based on the analysis.

According to an embodiment, the target data processing module 330 may predict the second target data (e.g., a target distance or a target duration) based on the source data (e.g., the first source data or the second source data) and the first target data. According to an embodiment, the target data processing module 330 may determine the second target data to predict, according to the type of the first target data determined. For example, if the first target data is calculated based on the distance, the second target data may be the target duration. If the first target data is calculated based on the duration, the second target data may be the target distance.

According to an embodiment, the target data processing module 330 may predict second target data based on various estimation schemes. For example, the target data processing module 330 may predict a plurality of corresponding target data, based on maximum oxygen consumption (Vo2Max) estimation based on the exercise data, maximum oxygen consumption estimation based on profile and test results, maximum oxygen consumption estimation based on external data (e.g., data measured and inputted by a wearable device), estimation based on Dave Cameron's model, or estimation based on Pete Riegel's model. The target data processing module 330 may predict the second target data based on the predicted target data.

According to an embodiment, the target data processing module 330 may perform regression analysis for the second target data. For example, the target data processing module 330 may determine the second target data using a linear regression model. According to an embodiment, the target data processing module 330 may determine the second target data using any one or a combination of the prediction and the regression for the second target data.

The recommendation data generating module 340 may generate recommendation data based on the second target data and the second target data. According to an embodiment, the recommendation data generating module 340 may generate the recommendation data by combining additional information (e.g., warm-up and cool-down periods) with the first target data and/or the second target data. In various embodiments, the additional data may be data regarding next exercise and may include, for example, at least one of duration or distance data corresponding to the warm-up and the cool-down.

According to an embodiment, the recommendation data generating module 340 may determine overfitting of the recommendation data based on the first target data and the second data, and modify (or process) the recommendation data based on the determination.

The guide module 350 may set (register) the generated recommendation data as one of exercise programs. Based on execution of the exercise program, the guide module 350 may feed various guides regarding a user's exercise status back to the user based on at least one of a visual sense, an auditory sense, or a tactile sense.

As such, an electronic device 101 according to various embodiments may include sensor circuitry (e.g., the sensor module 176) and a processor 120, wherein the processor 120 configured to determine at least one activity information which satisfies a designated condition among one or more activity information previously obtained in relation to a user motion, to determine a first exercise intensity for the user, based at least on variation of the at least one activity information over time, to determine a second exercise intensity by adjusting the first exercise intensity, based at least on a previous target of exercise of the user, and to provide guide information associated with the second exercise intensity.

According to various embodiments, the processor 120 may be configured to determine the first exercise intensity, further based on modification information by applying a designated weight to at least part of the at least one activity information.

According to various embodiments, the processor 120 may be configured to include, as at least part of the modification information, at least one of average workout distance information or average workout duration information determined based at least on the at least one activity information.

According to various embodiments, the processor 120 may be configured to set the target of exercise, based at least on biometric information of the user.

According to various embodiments, the electronic device 101 may further include communication circuitry (e.g., the communication module 190), and the processor 120 may be configured to transmit data of the determined second exercise intensity to an external electronic device is connected, using the communication circuitry.

According to various embodiments, the processor 120 may be configured to include, as at least part of the first exercise intensity and the second exercise intensity, at least one of a workout distance or a workout duration in relation to the target of exercise of the user.

According to various embodiments, the electronic device 101 may further include communication circuitry (e.g., the communication module 190), and the processor 120 may be configured to receive one or more activity information previously obtained in relation to the user motion, from an external electronic device which is connected, using the communication circuitry.

According to various embodiments, the processor 120 may be configured to modify the determined second exercise intensity, based at least on designated additional information.

According to various embodiments, the processor 120 may be configured to generate the guide information, based at least on whether the determined second exercise intensity satisfies a designated exercise intensity range.

According to various embodiments, the processor 120 may be configured to determine the at least one activity information based on a criteria number.

As stated above, an electronic device 101 according to various embodiments may include a display 210 and a processor 120, and the processor 120 may be configured to obtain source data from exercise data of previous exercise of a user, to determine first target data from at least part of the source data, to estimate a plurality of prediction results for second target data, using the source data and the first target data, to determine the second target data based on an average of the prediction results, and to generate recommendation data for exercise coach of the user based on the first target data and the second target data.

According to various embodiments, the processor 120 may be configured to filter the exercise data based on at least one condition.

According to various embodiments, the processor 120 may be configured to smooth the filtered exercise data, and to obtain a source duration and a source distance from a smoothing result.

According to various embodiments, the processor 120 may be configured to, if the filtered exercise data exceeds a criteria number, reduce by the criteria number based on recent exercise data.

According to various embodiments, the processor 120 may be configured to preset or determine a type of the first target data based on user preference.

According to various embodiments, the processor 120 may be configured to estimate the prediction results based on a plurality of different estimation schemes.

According to various embodiments, the processor 120 may be configured to determine the second target data based on a linear regression model using the exercise data.

According to various embodiments, the processor 120 may be configured to generate the recommendation data by combining additional data with at least part of the first target data and the second target data.

According to various embodiments, the processor 120 may be configured to process the recommendation data in response to determining overfitting of the recommendation data.

According to various embodiments, the processor 120 may be configured to register the recommendation data as an exercise program of the electronic device.

In the following, an operating method according to various embodiments of the present disclosure is explained by referring to the attached drawings. However, various embodiments of the present disclosure are not restricted by or limited to contents which will be described below and therefore, and it should be noted that they may be applied to various embodiments based on the embodiments to be described below. In various embodiments of the present disclosure described below, a hardware approach will be described as an example. However, since various embodiments of the present disclosure include a technology using both hardware and software, the various embodiments of the present disclosure do not exclude a software-based approach.

Figure 4:
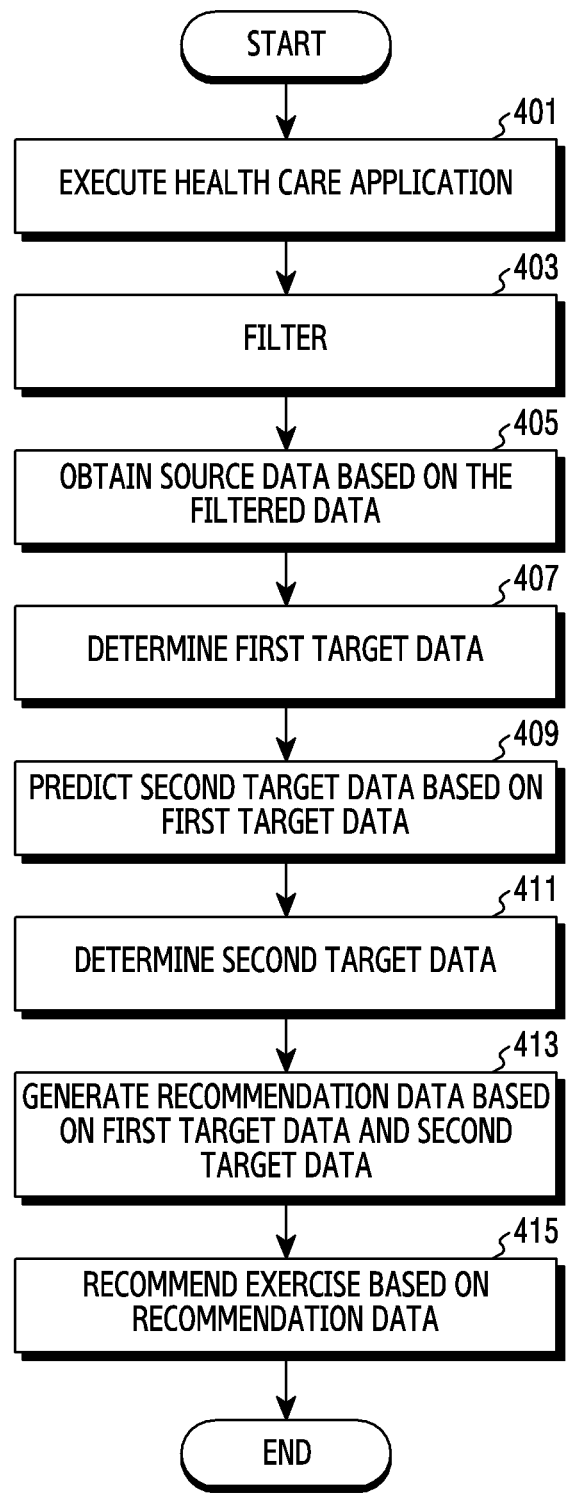
FIG. 4 is a flowchart of a method for providing a health care service in an electronic device according to various embodiments of the present disclosure.

FIG. 4 is a flowchart of a method for providing a health care service in an electronic device according to various embodiments of the present invention.

Referring to FIG. 4, in operation 401, one or more processors (or control circuitry (or the function processing module 300 of FIG. 3)) including the processor 120 (e.g., processing circuitry) of the electronic device 101 may execute a health care application. According to an embodiment, the processor 120 may determine the health care application execution, based on determining (or detecting) that the user requests (or selects or touches) the health care application execution using the electronic device 101.

In various embodiments, executing the health care application of operation 401 may be omitted in FIG. 4. According to an embodiment, in operation 401 of FIG. 4, the user may execute the health care application and finally use exercise data recommendation. According to an embodiment, if operation 401 of FIG. 4 is omitted, the electronic device 101 (or the processor 120) may autonomously generate exercise data to recommend for the user and provide the exercise data, in the form of a pop-up or a card, to the user, without executing the health care application. For example, the processor 120 may provide the recommended exercise data in the form of the pop-up or the card at a timing when the user often does the exercise (e.g., before the exercise).

According to various embodiments, the processor 120 may perform the operations of FIG. 4 based at least on the user's health care application execution or user history information (e.g., repeated exercise time).

In operation 403, the processor 120 may filter user's previous workout data stored. According to an embodiment, the processor 120 may extract workouts corresponding to a designated condition, from one or more workout logs of the user. According to an embodiment, if it is assumed that the designated condition includes a first condition (e.g., over 10 minutes) for the duration and a second condition (e.g., over one kilometers (km)) for the distance, the processor 120 may extract workouts included in (or satisfying) the first condition and the second condition among the workouts. According to an embodiment, the processor 120 may further set a condition of a particular duration (e.g., within the last month), and extract workouts included in the first condition and the second condition within the particular duration. According to an embodiment, the processor 120 may limit the number of the extracted workouts according to setting. For example, if the setting defines ten or fewer in number, the processor 120 may, if extracting more than ten workouts, determine the latest ten workouts.

In operation 405, the processor 120 may obtain source data based on the filtered workouts. In various embodiments, the source data may include data regarding the filtered workouts, for example, duration data and distance data. In various embodiments, for the sake of explanations, it is assumed that, but not limited to, first source data is the distance data and second source data is the duration data. It is noted that the first source data may be the duration data and the second source data may be the distance data.

In operation 407, the processor 120 may determine first target data based on the first source data. According to an embodiment, if the first source data is the distance data, the processor 120 may determine a target distance for a current timing, based on distance data of the filtered workouts. In various embodiments, determining the first target data (e.g., the target distance) shall be elucidated by referring to the drawings.

In operation 409, the processor 120 may predict (or estimate) second target data based on the source data (e.g., the first source data or the second source data) and the first target data. In various embodiments, the processor 120 may estimate the second target data based at least in part on various estimation schemes. In various embodiments, to estimate a more accurate value of the second target data, a plurality of different estimation schemes (e.g., workout performance prediction approaches) are used by way of example. For example, the processor 120 may estimate the second target data based on the plurality of the estimation schemes including a first estimation scheme, a second estimation scheme, a third estimation scheme, a fourth estimation scheme, and a fifth estimation scheme. According to an embodiment, in response to the plurality of the estimation schemes, the estimated second target data may estimate a plurality of target data corresponding to the estimation schemes. In various embodiments, estimating the second target data (e.g., the target duration) shall be elucidated by referring to the drawings.

In operation 411, the processor 120 may determine second target data. In various embodiments, the processor 120 may determine final second target data based on the multiple target data based on the estimation result. According to an embodiment, the processor 120 may determine the final second target data by calculating an average of the target data. According to an embodiment, the processor 120 may determine the second target data using a linear regression model. In various embodiments, determining the second target data shall be elucidated by referring to the drawings.

In operation 413, the processor 120 may generate recommendation data for exercise coach, based on the first target data and the second target data. According to an embodiment, the processor 120 may register a new exercise program based on the generated recommendation data. In various embodiments, generating the recommendation data shall be elucidated by referring to the drawings.

In operation 415, the processor 120 may recommend exercise based on the recommendation data. According to an embodiment, the processor 120 may provide (or initiate) the exercise coach (or guide) based on the recommendation data.

Figure 5:
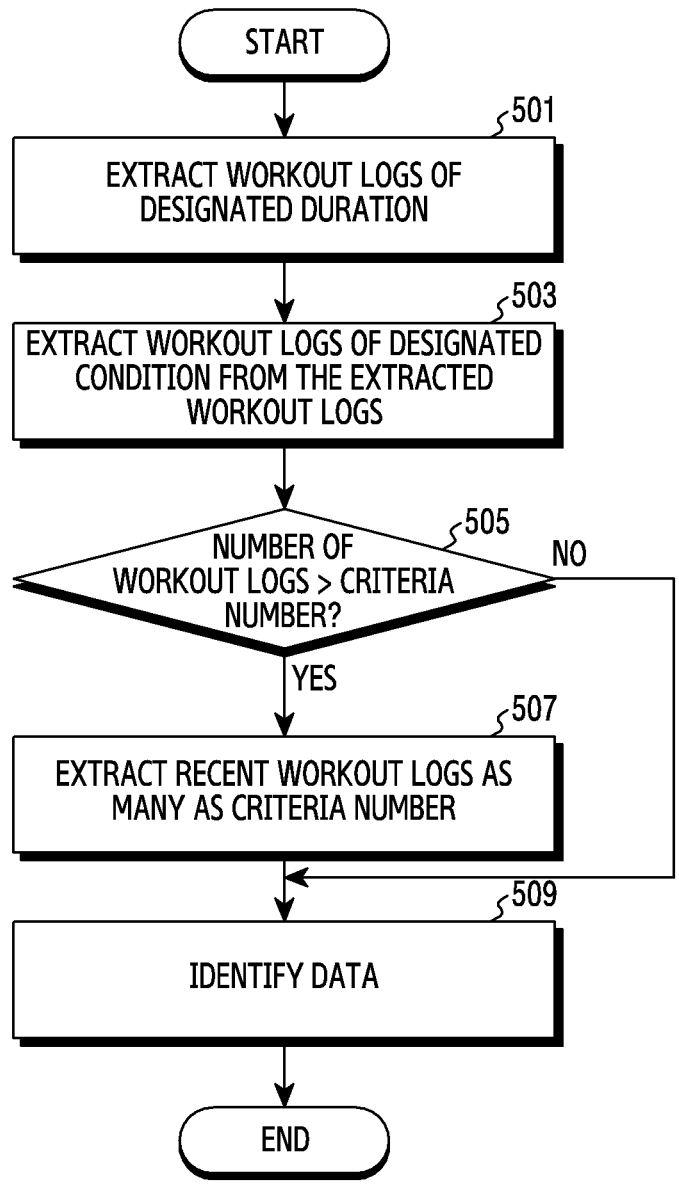
FIG. 5 is a flowchart of a filtering method in an electronic device according to various embodiments of the present disclosure.

FIG. 5 is a flowchart of a filtering method in an electronic device according to various embodiments of the present disclosure.

Referring to FIG. 5, in operation 501, the processor 120 of the electronic device 101 may extract first workout logs of a specific duration among workout logs stored. According to an embodiment, the processor 120 may extract workout logs of a specific duration (e.g. within the last month from today) from at least one workout log of the user. According to an embodiment, the at least one workout log may include a log measured by at least one of the sensor module 176 or the communication module 190 (e.g., position determining circuitry, for example, a global navigation satellite system (GNSS) or a global positioning system (GPS)) of the electronic device 101 during the user's exercise, and a log inputted by the user through an input device.

In operation 503, the processor 120 may extract second workout logs of a specific condition from the first workout logs extracted. In various embodiments, a plurality of conditions may be set. According to an embodiment, the condition may include a first condition (e.g., over 10 minutes) for the duration and a second condition (e.g., over 1 km) for the distance. The processor 120 may extract the second workout logs corresponding to the first condition and the second condition from the first workout logs.

In operation 505, the processor 120 may determine whether the number of the extracted second workout logs exceeds a criteria number. According to an embodiment, if the criteria number is smaller than 10, the processor 120 may determine whether the number of the extracted second workout logs exceeds 10.

If determining that the number of the extracted second workout logs does not exceed 10 in operation 505, for example, if determining that the number of the second workout logs falls below the criteria number, the processor 120 may proceed to operation 509.

If determining that the number of the second workout logs exceeds 10 in operation 505, the processor 120 may extract third workout logs as many as the criteria number from the second workout logs based on a recent workout log in operation 507. According to an embodiment, the processor 120 may extract ten third workout logs from the extracted second workout logs by counting the criteria number (e.g., 10) based on the latest workout log.

In operation 509, the processor 120 may identify data based on the filtered third workout logs. For example, the electronic device 120 may identify source data based on ten workout logs.

FIGS. 6A and 6B are diagrams of an example of filtering results in an electronic device according to various embodiments.

FIG. 6A depicts an example for distinguishing data of a specific duration (e.g., within the latest one month from today) among user's workouts (or workout logs) stored (or recorded) in the electronic device 101. According to an embodiment, FIG. 6A may correspond to the first workout logs described above in FIG. 5.

FIG. 6B depicts an example for distinguishing data of the first condition (e.g., exercise over 10 minutes) and the second condition (e.g., exercise over 1 km) among the user's workouts (or workout logs) stored (or recorded) in the electronic device 101. According to an embodiment, FIG. 6B may correspond to the second workout logs described above in FIG. 5.

While the data is filtered based on the particular duration and the second condition (e.g., the distance condition) in FIGS. 6A and 6B to facilitate the explanations, the first condition (e.g., the duration condition) may be considered together as mentioned earlier.

Figure 6:
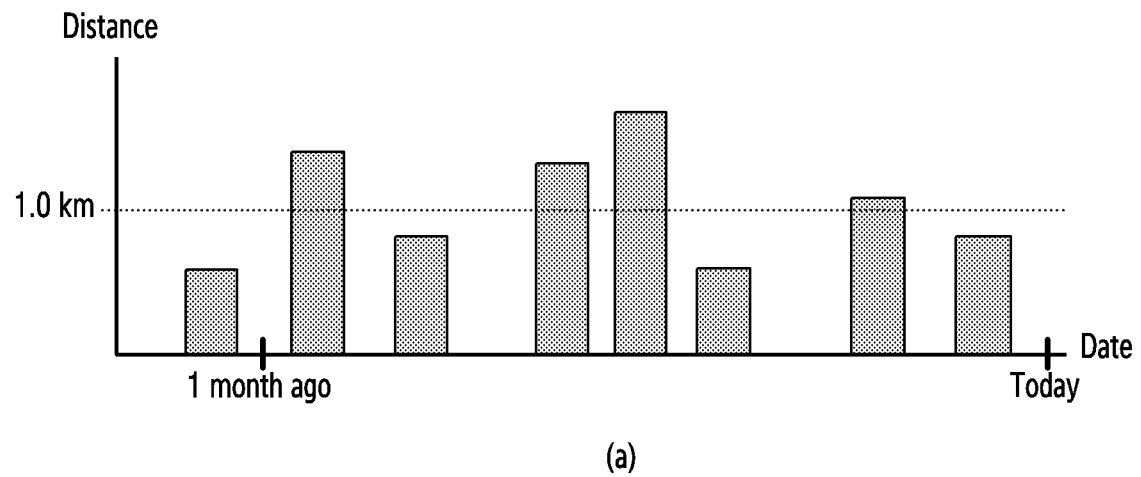
FIGS. 6A and 6B are diagrams of an example of filtering results in an electronic device according to various embodiments.
Figure 6:
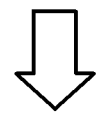
Figure 6:
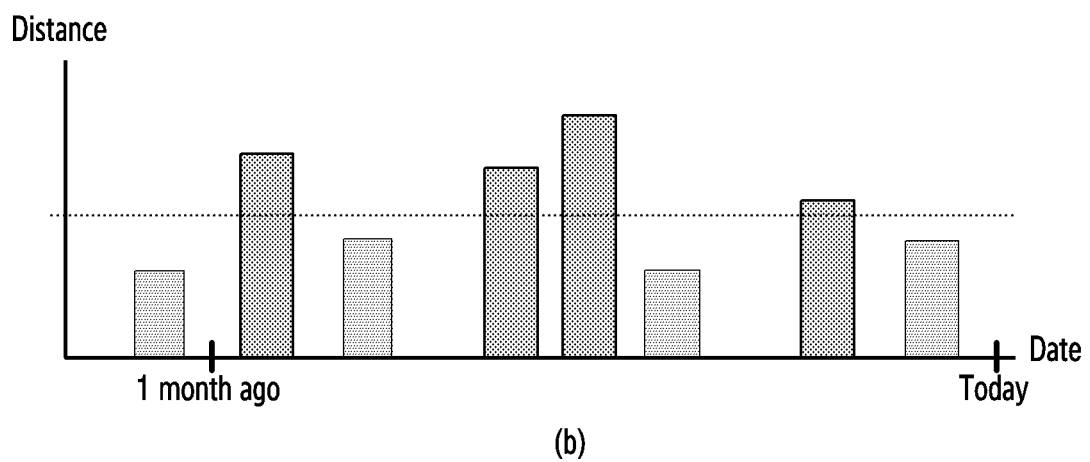

As shown in FIG. 5 and FIG. 6, various embodiments may select criteria data used to obtain target data for recommending next exercise by filtering the workout data. In various embodiments, the selected criteria data may be data for improving reliability of the target data.

Figure 7:
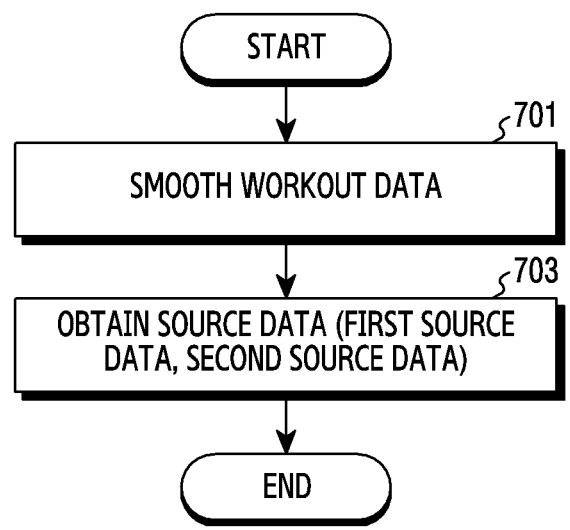
FIG. 7 is a flowchart of a method for obtaining source data in an electronic device according to various embodiments.
Figure 8:
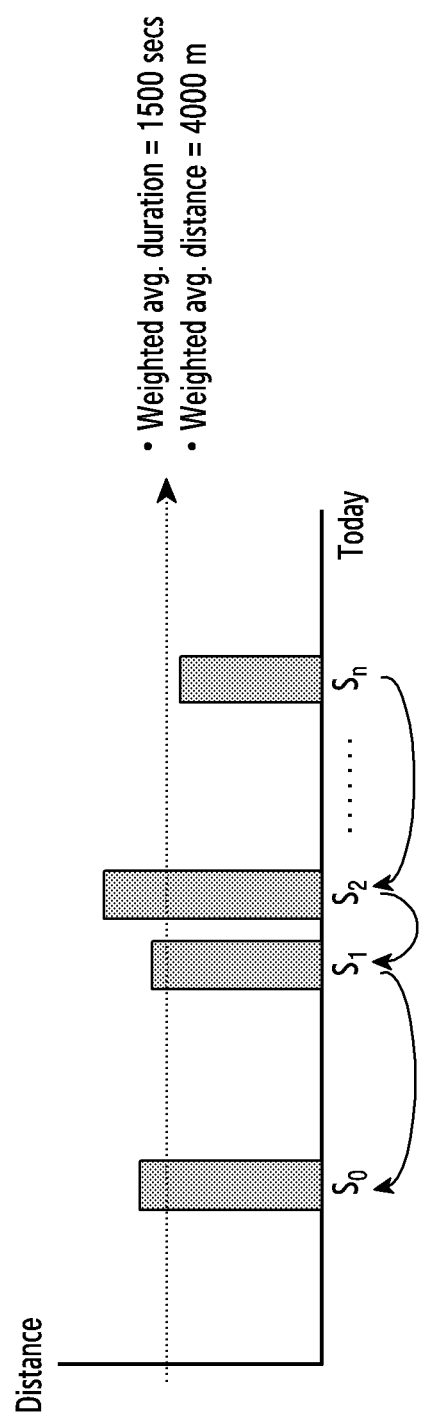
FIG. 8 is a diagram of an example for obtaining source data in an electronic device according to various embodiments.

FIG. 7 is a flowchart of a method for obtaining source data in an electronic device according to various embodiments. FIG. 8 is a diagram of an example for obtaining source data in an electronic device according to various embodiments.

Referring to FIG. 7, in operation 701, the processor 120 of the electronic device 101 may smooth workout data using a specific prediction scheme. According to an embodiment, the workout log (e.g., filtered data) may be time series data. In various embodiments, the prediction scheme adopts, but not limited to, the exponential smoothing. According to an embodiment, the exponential smoothing may be an example of weighted moving average prediction schemes which assign the greatest weight to the most recent data of the time series data and exponentially decrease the weight over time. For example, the exponential smoothing may calculate an average using every time series data and predict data by assigning a greater weight to recent time series data over time. According to an embodiment, the processor 120 may calculate source data (e.g., first source data or second source data) by substituting workout data (e.g., duration data or distance data) per workout log into the exponential smoothing. Equation 1 expresses a formula example of the exponential smoothing.

$$s_0 = x_0$$

$$s_t = \alpha x_t + (1-\alpha) s_{t-1}, \ t > 0 \quad (1)$$

In Equation 1, $s_t$ may denote the exponential smoothing at time t, $x_t$ may denote source data at the time t, and $\alpha$ may indicate a smoothing factor (or weight). According to an embodiment, the smoothing factor may be predetermined or adaptively determined. For example, the smoothing factor may have a value of $0<\alpha<1$, and mostly use $0.1<\alpha<0.3$. In various embodiments, the smoothing factor is 0.3 by way of example, to increase the weight on the recent source data.

In operation 703, the processor 120 may obtain source data (e.g., first source data or second source data) based on the smoothing result according to the prediction scheme, which is shown in FIG. 8. As shown in FIG. 8, the first source data is determined to 4000 m (e.g., weighted average distance=4000 m) and the second source data is determined to 1500 secs (e.g., weighted average duration=1500 secs).

Figure 9:
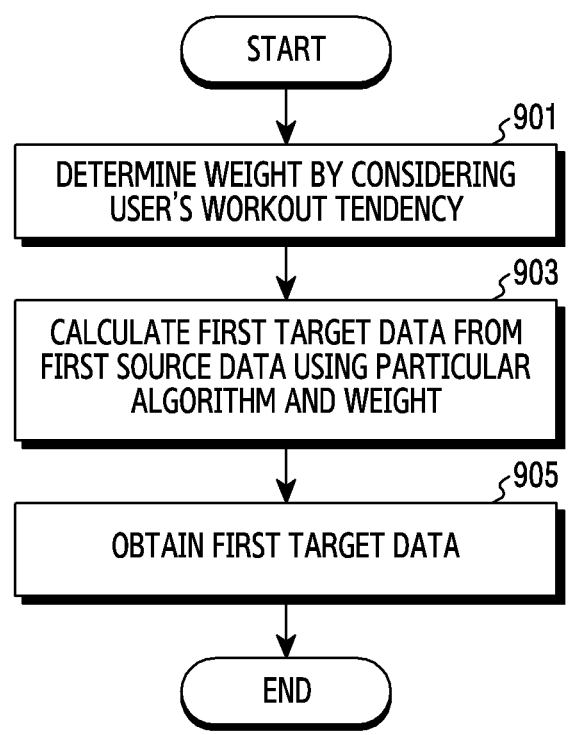
FIG. 9 is a flowchart of a method for determining target data in an electronic device according to various embodiments.
Figure 10:
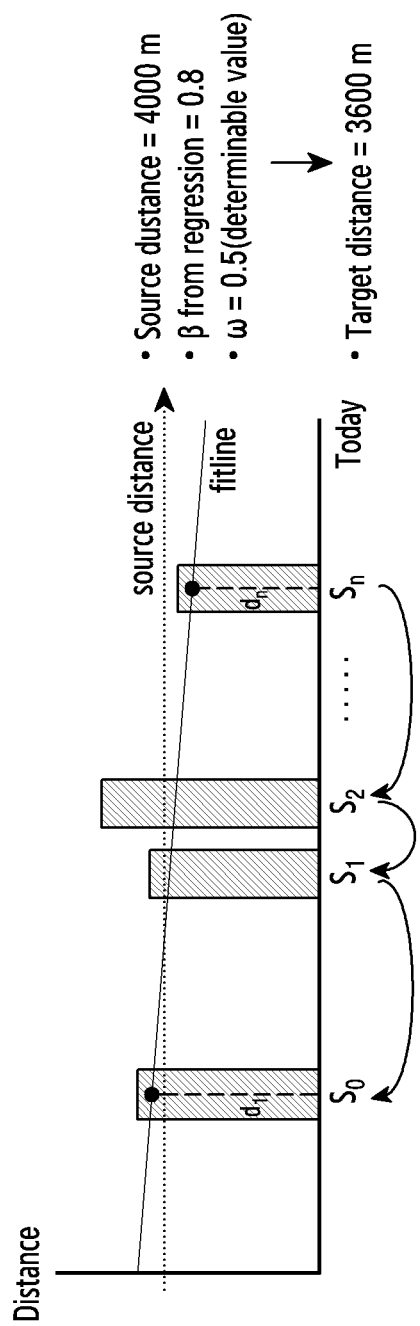
FIG. 10 is a diagram of an example for determining target data in an electronic device according to various embodiments.

FIG. 9 is a flowchart of a method for determining target data in an electronic device according to various embodiments. FIG. 10 is a diagram of an example for determining target data in an electronic device according to various embodiments.

Referring to FIG. 9, in operation 901, the processor 120 of the electronic device 101 may determine a weight (or a weight ratio) by considering user's workout tendency. According to an embodiment, the weight for the user's workout tendency may be determined by determining the user's workout tendency based on user's previous workout data (e.g., exercise distance) and considering its increase or decrease. In various embodiments, the weight is 0.5 by way of example.

In operation 903, the processor 120 may calculate first target data from first source data using a particular algorithm and the weight. In various embodiments, the particular algorithm adopts, but not limited to, the linear regression analysis. The linear regression analysis may, in general, indicate the regression analysis scheme which models linear relationship of a dependent variable y and one or more independent variables (or explanatory variables) x. For example, the linear regression equation of Equation 2 may be used to predict the value y (e.g., first target data) for the value x (e.g., first source data) having no y (e.g., first target data). Equation 2 expresses an example of a formula for targeting the first target data.

$$d_i = t_i\beta + \varepsilon_i, \quad i = 1, \ldots, n, \qquad (2)$$
$$d_t = d_s \times \frac{d_n}{d_1}\omega$$

In operation 905, the processor 120 may obtain the first target data based on the calculation result. According to an embodiment, the processor 120 may obtain a target distance which is the first target data, based on distance data which is the first source data, which is depicted in FIG. 10. As shown in FIG. 10, the first target data (e.g., the target distance) is determined to 3600 m based on the first source data (e.g., 4000 m) determined in FIG. 8, a slope β (e.g., 0.8) of a fit line acquired through the regression analysis, and a weight ω (e.g., 0.5).

Figure 11:
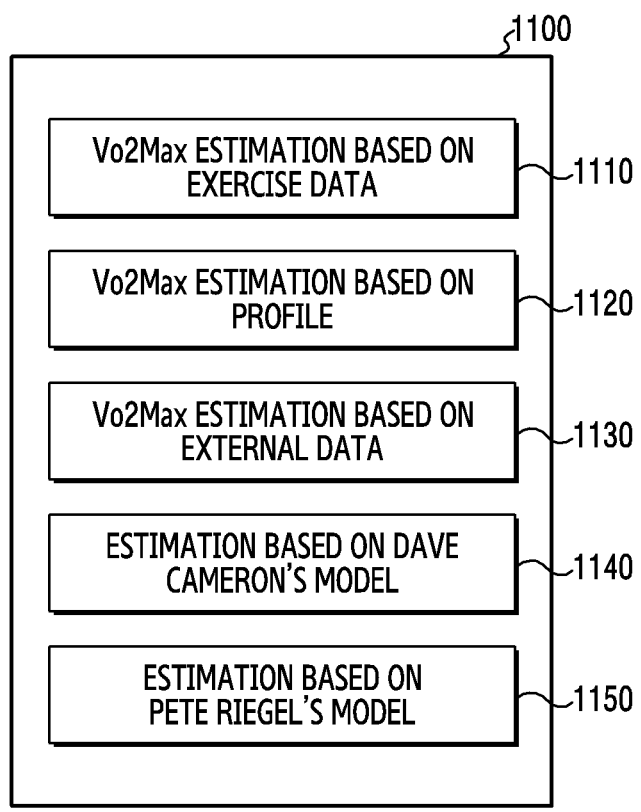
FIG. 11 is a diagram of an example of a method for estimating target data in an electronic device according to various embodiments.

FIG. 11 is a diagram of an example of a method for estimating target data in an electronic device according to various embodiments.

As shown in FIG. 11, various embodiments may use a plurality of estimation schemes, as a method 1100 for predicting and estimating target data. For example, the estimation schemes may include a scheme 1110 for estimating the target data by calculating a maximum oxygen consumption (Vo2Max) based on exercise data, a scheme 1120 for estimating the target data by calculating the maximum oxygen consumption based on profile and test result (e.g., 1.5 mile-test result), a scheme 1130 for estimating the target data by calculating the maximum oxygen consumption based on external data (e.g., data measured and inputted by a wearable device), a scheme 1140 for estimating the target data using Dave Cameron's model, or a scheme 1150 for estimating the target data using Pete Riegel's model. In various embodiments, in response to the estimation schemes, a plurality of target data (e.g., second target data) corresponding to the estimation schemes may be estimated.

Examples of the estimation schemes used in various embodiments are represented as follows. The estimation schemes are well-known performance predictors and their detailed descriptions shall be omitted here.

According to an embodiment, the estimation 1110 using the maximum oxygen consumption based on the exercise data may predict the target data based on Equation 3.

$$p_{max} = 0.8 + 0.1894393e^{-0.012778t} + 0.2989558e^{-0.1932605t} \qquad (3)$$
$$vo_2 = -4.60 + 0.1822588v + 0.000104v^2$$
$$V_{O_2}\text{Max} = \frac{vo_2}{p_{max}}$$

In Equation 3, the time may be based on minutes, and the velocity may be based on meters per minute. For example, Equation 3 may be used to calculate the time in response to the well-known maximum oxygen consumption and the distance.

According to an embodiment, the estimation 1120 using the maximum oxygen consumption based on the profile and the test result may predict the target data based on Equation 4.

$$V_{O_2}\text{Max} = 88.02 + \left(3.716 \times \left\{ \begin{array}{l} 1 \text{ (for male)} \\ 0 \text{ (for female)} \end{array} \right\} \right) - 0.753w - 2.767t \qquad (4)$$

In Equation 4, w may denote the weight (lb) and t may denote 1.5 mile time. For example, Equation 4 may be used to calculate the time in response to the well-known maximum oxygen consumption and the distance.

According to an embodiment, the estimation 1130 using the maximum oxygen consumption based on the external data may receive data about the maximum oxygen consumption from an external device (e.g., a wearable device) associate (or coupled) with the electronic device 101, and predict data for deriving maximum oxygen consumption which approximately matches the inputted maximum oxygen consumption.

According to an embodiment, the estimation 1140 using Dave Cameron's model may predict the target data based on Equation 5.

$$a = 13.49681 - 0.000030363d_1 + \frac{835.7114}{d_1^{0.7905}} \qquad (5)$$
$$b = 13.49681 - 0.000030363d_2 + \frac{835.7114}{d_2^{0.7905}}$$
$$t_2 = \frac{t_1}{d_1} \times \frac{a}{b} \times d_2$$

In Equation 5, $t_1$ may denote a source duration (e.g., second source data), $t_2$ may denote a target duration (e.g., second target data), $d_1$ may denote a source distance (e.g., first source data), and $d_2$ may denote a target distance (e.g., first target data).

The estimation 1150 using Pete Riegel's model may predict the target data based on Equation 6.

$$t_2 = t_1 \times \left(\frac{d_2}{d_1}\right)^{1.06} \qquad (6)$$

In Equation 6, $t_1$ may denote the source duration (e.g., second source data), $t_2$ may denote the target duration (e.g., second target data), $d_1$ may denote the source distance (e.g., first source data), and $d_2$ may denote the target distance (e.g., first target data).

According to various embodiments, in response to the plurality of the estimation schemes, a plurality of target data corresponding to the estimation schemes may be estimated. According to various embodiments, final target data (e.g., the second target data of FIG. 4) may be determined based at least in part on the plurality of the target data according to the estimation results, which is illustrated in FIG. 12.

Figure 12:
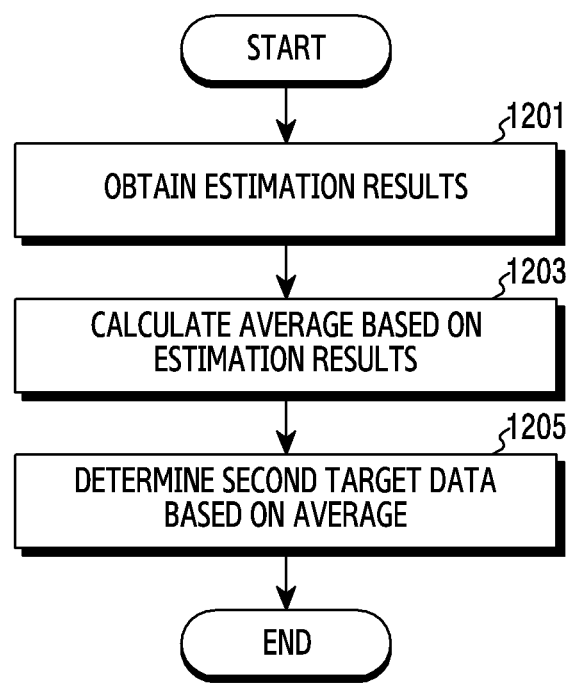
FIG. 12 is a flowchart of a method for determining target data in an electronic device according to various embodiments.

FIG. 12 is a flowchart of a method for determining target data in an electronic device according to various embodiments.

Referring to FIG. 12, in operation 1201, the processor 120 of the electronic device 101 may obtain estimation results. According to an embodiment, the processor 120 may obtain the results (e.g., the plurality of the target data) estimated based on the estimation schemes (e.g., the first estimation scheme through the fifth estimation scheme) as stated in FIG. 11.

In operation 1203, the processor 120 may calculate an average based on the estimation results. According to an embodiment, the processor 120 may calculate the average of the estimation results (e.g., the plurality of the target data) of the first estimation scheme through the fifth estimation scheme.

In operation 1205, the processor 120 may determine the calculated average as second target data. According to an embodiment, referring back to FIG. 11, the processor 120 may determine 57 minutes 5 seconds (e.g., 3425 secs) as the second target data which is the target duration.

Referring to FIG. 11 and FIG. 12, practical examples are shown as follows.

TABLE 1

| Date | Duration | Distance |
|---|---|---|
| 4/24 | 60 minutes | 10 Km |
| 4/23 | 55 minutes | 9.5 Km |
| 4/22 | 50 minutes | 9 Km |

TABLE 2

| Estimation scheme | Predicted target data (e.g., target duration) | Final target data (average) |
|---|---|---|
| the first estimation scheme | 57:12 (3432 secs) | Avg. 54:05 (3425 secs) |
| the second estimation scheme | 57:01 (3421 secs) | |
| the third estimation scheme | 57:05 (3425 secs) | |
| the fourth estimation scheme | 57:13 (3433 secs) | |
| the fifth estimation scheme | 57:14 (3434 secs) | |

According to an embodiment, Table 1 shows exercise data stored. For example, Table 1 shows examples of exercise (exercise per date) conducted and filtered by the user, and source data (e.g., first source data (e.g., duration) and second source data (e.g., distance)) corresponding to the exercise.

According to an embodiment, Table 2 shows examples of target data (e.g., target durations) estimated (predicted) for the second target data by applying the exercise data of Table 1 and the first target data (e.g., distance data) previously obtained, to the estimation schemes (e.g., the first estimation scheme through the fifth estimation scheme). According to various embodiments, an average may be calculated with the predicted target data, and the calculated average may be determined as final target data (e.g., the second target data, for example, target duration data).

Figure 13:
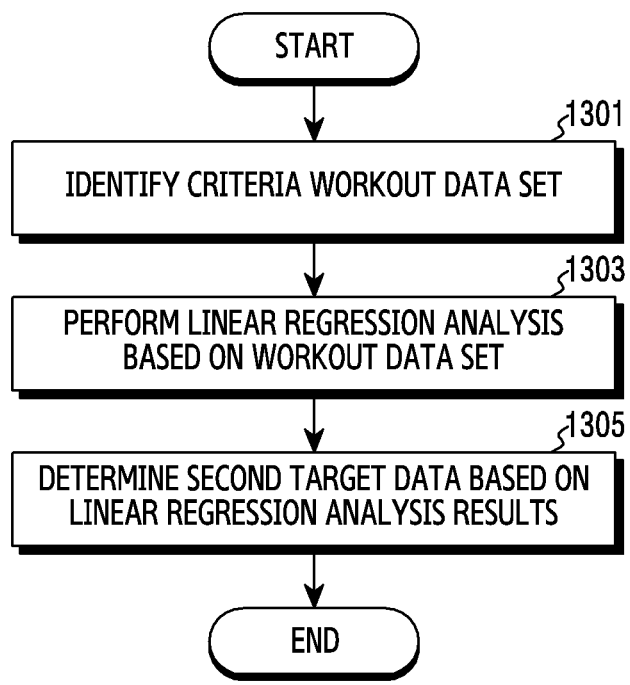
FIG. 13 is another flowchart of a method for determining target data in an electronic device according to various embodiments.
Figure 14:
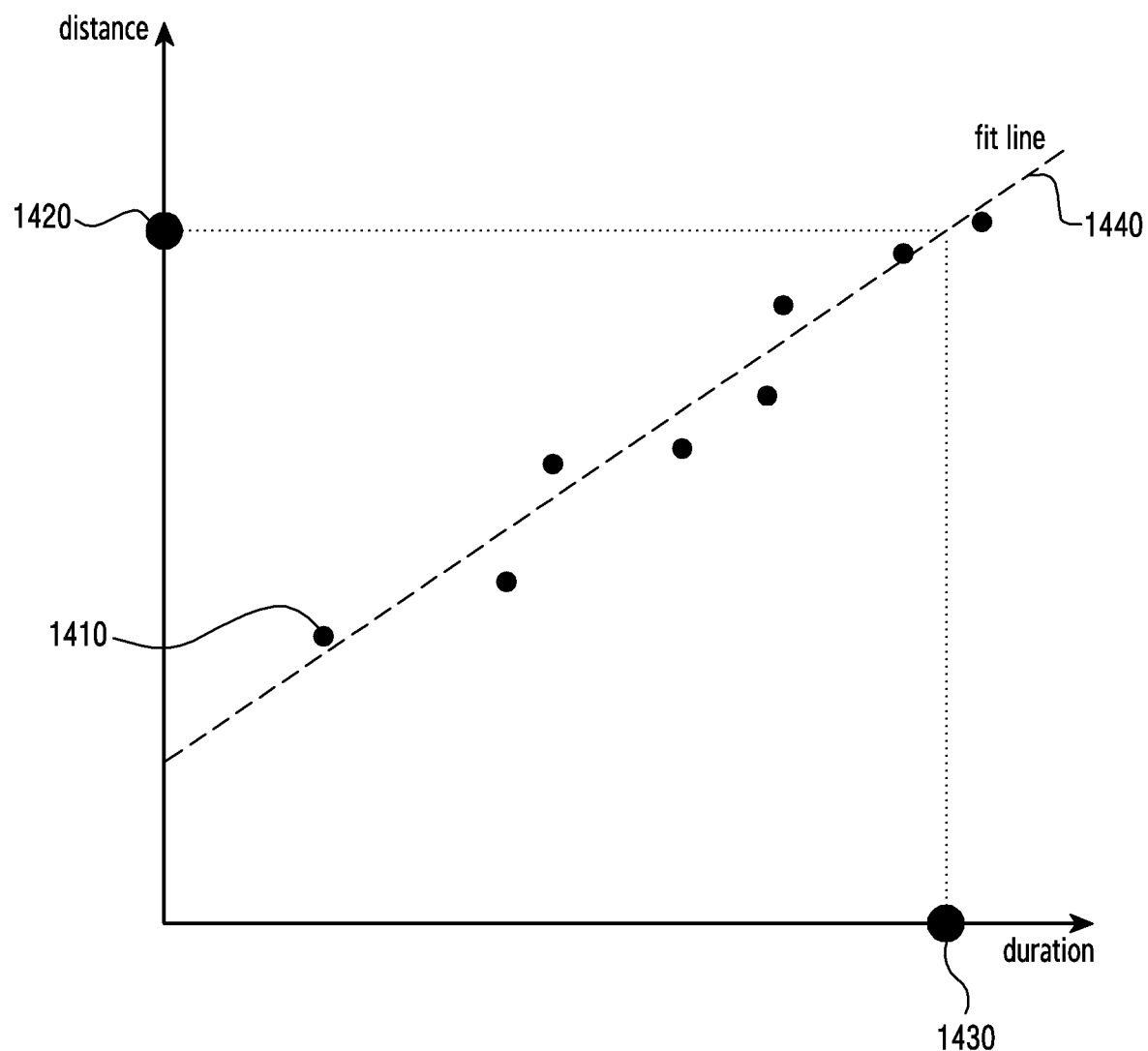
FIG. 14 is a diagram of another example for determining target data in an electronic device according to various embodiments.

According to various embodiments, the target data may be determined using the linear regression analysis according to linearity of the exercise data, without or in addition to the prediction using the estimation schemes, which shall be described by referring to FIG. 13 and FIG. 14.

FIG. 13 is another flowchart of a method for determining target data in an electronic device according to various embodiments. FIG. 14 is a diagram of another example for determining target data in an electronic device according to various embodiments.

Referring to FIG. 13, in operation 1301, the processor 120 of the electronic device 101 may identify a criteria workout data set. According to an embodiment, the processor 120 may identify (or extract) the workout data set as mentioned in Table 1. For example, the workout data set may be obtained with the data of Table 1 based on Equation 7.

$$D=\{duration_i, distance_i\}_{i=1}^{n} \quad (7)$$

In operation 1303, the processor 120 may perform the linear regression analysis based on the workout data set. For example, the processor 120 may obtain a regression coefficient (e.g., an intercept coefficient or a slope coefficient), based on the given workout data set, which is shown in FIG. 14.

As shown in FIG. 14, an element 1410 may indicate workout logs according to the given workout data set, an element 1420 may indicate a target distance, an element 1430 may indicate a target duration, and an element 1440 may indicate a fit line (or a regression line). For example, in FIG. 14, the intercept coefficient (e.g., y-intercept) is 55 and the slope coefficient is 0.85 based on Equation 8.

$$y=0.85x+55 \quad (8)$$

In various embodiments, second target data (e.g., the target duration) may be calculated by substituting first target data (e.g., the target distance, the value x in Equation 8) into the linear regression analysis, which is expressed, for example, as Equation 9. According to an embodiment, in Equation 9, the target distance as the first target data is 3600 as illustrated in FIG. 9 and FIG. 10.

$$y=(0.85\times 3600)+55=3115 \quad (9)$$

In operation 1305, the processor 120 may determine the second target data, based on the result of the linear regression analysis. According to an embodiment, the processor 120 may determine the calculated "3115" as the second target data (e.g., the target duration) according to the result of Equation 9.

According to various embodiments, as stated in FIG. 11 through FIG. 14, with respect to the predicted (or estimated) target data, the results of all the approaches (e.g., the prediction (estimation) schemes) may be combined using a weight function according to the purpose. According to an embodiment, the results may be combined based on the formula of Equation 10.

$$t_f = \omega \begin{pmatrix} \varphi_1 f_1(d_s, d_t, t_s) + \\ \varphi_2 f_2(d_s, d_t, t_s) + \\ \varphi_3 f_3(d_s, d_t, t_s) + \\ \varphi_4 f_4(d_s, d_t, t_s) + \\ \varphi_5 f_5(d_s, d_t, t_s) \end{pmatrix} + (1-\omega)(g(d_s, d_t, t_s)) \quad (10)$$

In Equation 10, $\varphi_1+\varphi_2+\varphi_3+\varphi_4+\varphi_5=1$, $f_1$, $f_2$, $f_3$, $f_4$, and $f_5$ may denote estimation functions corresponding to the estimation schemes (e.g., the first estimation scheme 1110 through the fifth estimation scheme 1150), g may denote a regression function, $d_s$ may denote a source distance, $d_t$ may denote a target distance, $t_s$ may denote a source duration, $t_f$ may denote a final target duration, and $\varphi$ and $\omega$ may denote weight factors.

According to various embodiments, basic criteria for determine the weight factors $\omega$ and $\varphi_k$ may be set as follows.

According to an embodiment, the weight factor $\omega$ is to determine the prediction vs the regression. For example, if a difference of the workout data is not relatively great, $\omega$ may be selected as a smaller value because the regression result is stable according to the data distribution, and vice versa.

According to an embodiment, the weight factor $\varphi_k$ is to determine importance among the prediction models. For example, if there is proper profile data from a user input, great values (e.g., $\varphi_1=0.25$, $\varphi_2=0.25$, $\varphi_3=0.25$) may be assigned to $\varphi_1$, $\varphi_2$, and $\varphi_3$ because the Vo2Max estimation may return a better result when the profile data is used for the calculation parameter. For example, a high weight may be set to the Vo2Max estimation scheme (e.g., the first estimation scheme 1110, the second estimation scheme 1120, and the third estimation scheme 1130) calculable based on the profile. According to an embodiment, if the user profile information and additional input parameters are relatively inaccurate comparing to the previous case, a better result may be obtained by assigning a greater value (e.g., $\varphi_4=0.35$, and $\varphi_5=0.35$) to $\varphi_4$ and $\varphi_5$. For example, a high weight may be given to the model based estimation scheme (e.g., the fourth estimation scheme 1140, the fifth estimation scheme 1150).

According to an embodiment, provided that the sum of the weight factors is 1 (e.g., $\varphi_1+\varphi_2+\varphi_3+\varphi_4+\varphi_5=1$), if reliability of the user profile is high, a relatively high weight (e.g., sum=0.7) may be assigned to the Vo2Max estimation and a relatively low weight (e.g., sum=0.3) may be assigned to the model based estimation. According to an embodiment, if the reliability of the user profile is low, a relatively low weight (e.g., sum=0.3) may be assigned to the Vo2Max estimation and a relatively high weight (e.g., sum=0.7) may be assigned to the model based estimation, which shall be described by referring to FIG. 17.

Figure 15:
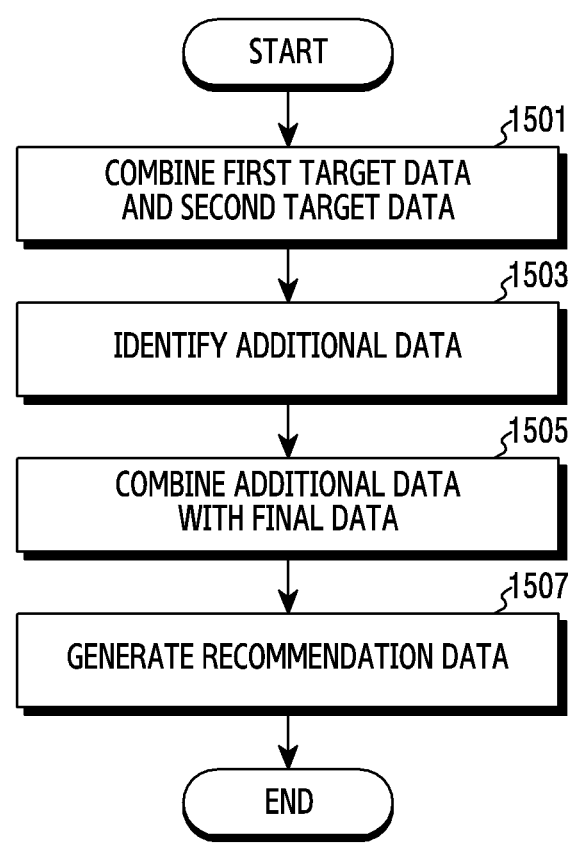
FIG. 15 is a flowchart of a method for generating recommendation data in an electronic device according to various embodiments.

FIG. 15 is a flowchart of a method for generating recommendation data in an electronic device according to various embodiments.

Referring to FIG. 15, in operation 1501, the processor 120 of the electronic device 101 may combine first target data and second target data, as one data set. According to an embodiment, the processor 120 may combine the set of the results from the estimations based on the various estimation schemes, and obtain final data including a final target duration and a final target distance for next exercise.

In operation 1503, the processor 120 may identify additional data. In various embodiments, the additional data is data about the next exercise, and may include, for example, at least one of duration or distance data corresponding to warm-up and cool-down.

In operation 1505, the processor 120 may combine (add) the additional data with the obtained final data. For example, the processor 120 may modify the obtained final data with the additional data. According to an embodiment, provided that the target exercise duration according to the final data is 10 minutes, exercise guide information of 20 minutes in total by adding 5 minutes (warm-up) before the exercise and 5 minutes (cool-down) after the exercise may be provided to the user.

According to an embodiment, the processor 120 may combine the additional data with at least one of the final data. According to an embodiment, the final data may include first target data (e.g., target distance) and second target data (e.g., target duration), and the processor 120 may combine the additional data with the first target data or the second target data according to the type of the recommendation data. According to an embodiment, if the recommendation data is based on the distance, the processor 120 may combine the first target data (e.g., target distance) with the additional data (e.g., a warm-up distance or a cool-down distance). According to an embodiment, if the recommendation data is based on the duration, the processor 120 may combine the second target data (e.g., target duration) with the additional data (e.g., a warm-up duration or a cool-down duration), which shall be explained by referring to FIG. 19.

In operation 1507, the processor 120 may generate recommendation data based on the combining result.

Figure 16:
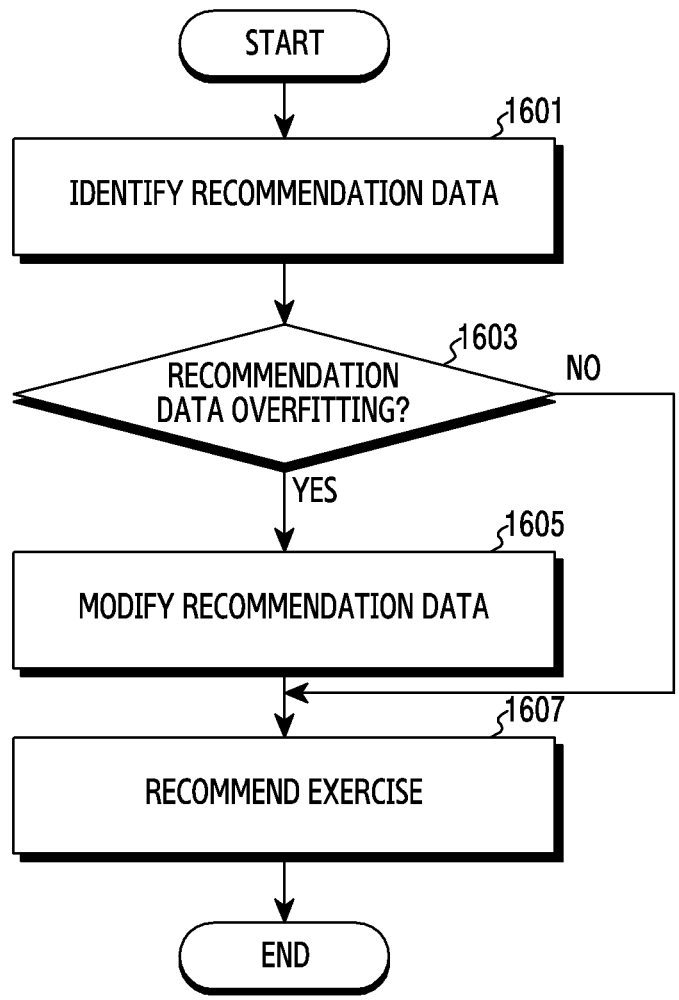
FIG. 16 is a flowchart of a method for processing recommendation data in an electronic device according to various embodiments.

FIG. 16 is a flowchart of a method for processing recommendation data in an electronic device according to various embodiments.

Referring to FIG. 16, the processor 120 of the electronic device 101 may identify generated recommendation data in operation 1601, and determine whether the recommendation data corresponds to overfitting in operation 1603. According to an embodiment, the processor 120 may compare the predicted recommendation data (e.g., target distance and target duration) for the next exercise with maximum data (e.g., maximum distance) of criteria exercise (e.g., exercise data measured by the electronic device 101 during the actual exercise of the user among previous exercise data of the user). According to an embodiment, the criteria exercise may not include exercise data manually inputted by the user. According to an embodiment, the processor 120 may determine the overfitting according to whether the recommendation data is greater than a preset criteria distance (e.g., a product of the maximum distance of the input workout and a particular multiple (e.g., 1.1 times)) based on Equation 11.

$$\text{recommendation data} > 1.1 \times \text{max.distanceofinputworkout} \quad (11)$$

If determining no overfitting of the recommendation data in operation 1603, the processor 120 may proceed to operation 1607.

If determining the overfitting of the recommendation data in operation 1603, the processor 120 may modify the recommendation data in operation 1605. According to an embodiment, if determining that the exercise distance (e.g., target distance) for the next exercise exceeds predefined distance criteria, the processor 120 may modify the recommendation data (e.g., first target data or second target data) based on a preset criteria value. According to an embodiment, the target distance and the target duration according to the first target data and the second target data may be reduced by the criteria value, based on the criteria value.

In operation 1605, the processor 120 may recommend exercise based on the modified recommendation data. According to an embodiment, recommending the exercise shall be described by referring to FIG. 18 and FIG. 19.

Figure 17:
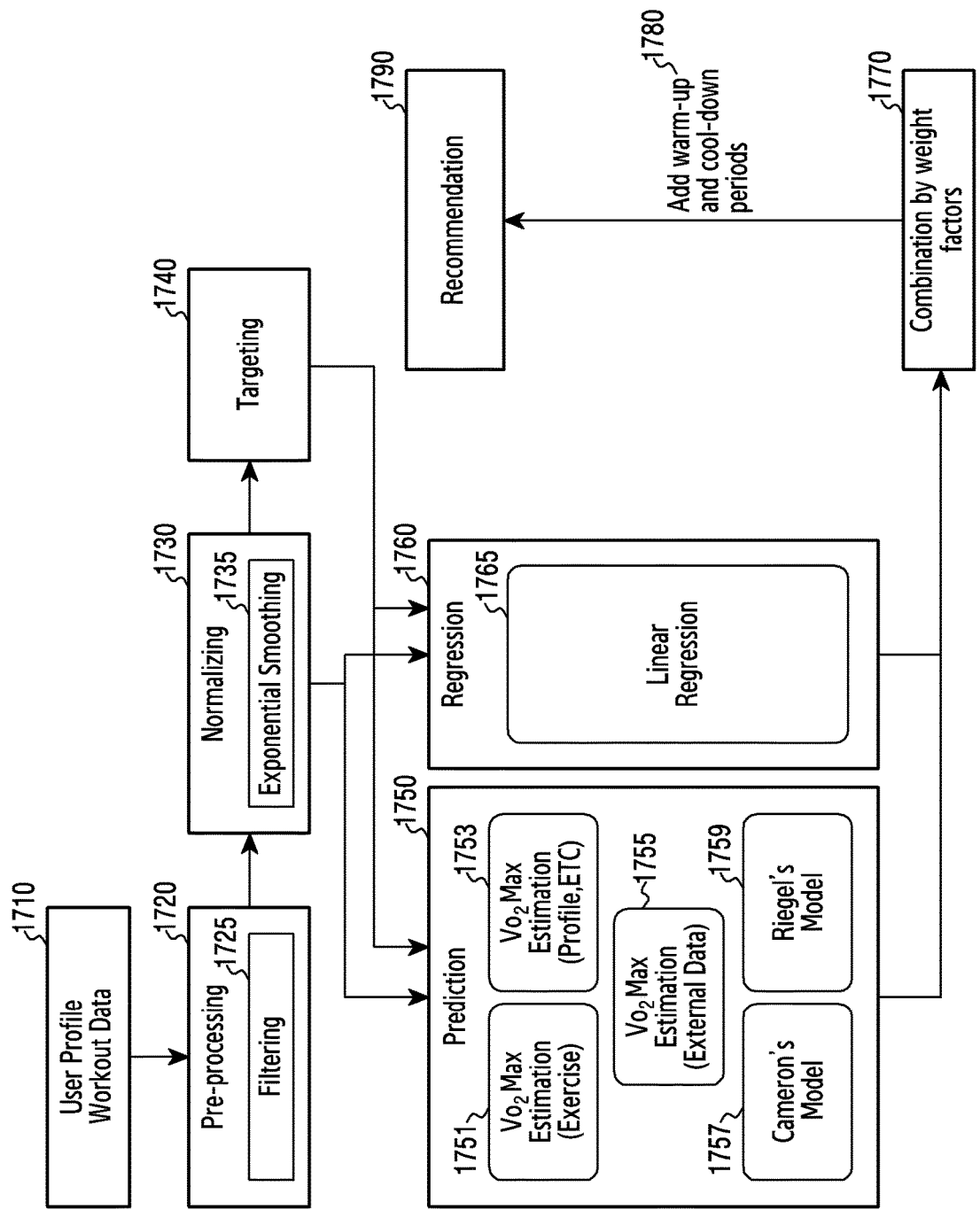
FIG. 17 is a diagram of a scenario for coaching exercise in an electronic device according to various embodiments.

FIG. 17 is a diagram of a scenario for coaching exercise in an electronic device according to various embodiments.

Referring to FIG. 17, in an element 1710, the electronic device 101 may obtain user profile and workout data. According to an embodiment, the user profile may be information pre-inputted by the user using the electronic device 101, and the workout data may include past workout data of the user and workout data inputted by the user.

In an element 1720, the electronic device 101 may perform pre-processing. According to an embodiment, the electronic device 101 may perform workout data filtering 1725 as the pre-processing operation. According to an embodiment, the electronic device 101 may conduct the filtering based on at least one preset condition. For example, at least one condition may include a period (e.g., a weekly, monthly, or yearly basis based on today) of the exercise data to extract, and at least one criteria condition (e.g., over a specific distance or over a specific duration) of the workout data, and the like.

In an element 1730, the electronic device 101 may perform normalizing. According to an embodiment, the electronic device 101 may, as the normalizing operation, smooth the workout data filtered using exponential smoothing 1735. According to an embodiment, the electronic device 101 may obtain source data (e.g., first source data or second source data) as the smoothing result.

In an element 1740, the electronic device 101 may target target data. According to an embodiment, the electronic device 101 may determine first target data (e.g., target distance or target duration) using the source data obtained using the smoothing. According to an embodiment, determining the first target data based on the source data may be selected by preset any one of the distance or the duration or based on user preference. According to an embodiment, if the set data is the distance, the electronic device 101 may calculate the target distance, as the first target data, based on the source data. According to an embodiment, if the set data is the duration, the electronic device 101 may calculate the target duration, as the first target data, based on the source data. According to an embodiment, the electronic device 101 may analyze the user preference (or tendency) based on the user profile, and calculate the target distance or the target duration, as the first target data, based on the analysis.

In an element 1750, the electronic device 101 may predict the target data. According to an embodiment, the electronic device 101 may predict second target data (e.g., target distance or target duration) based on the source data (e.g., the first source data or the second source data) and the first target data. According to an embodiment, the second target data to predict may be determined according to the determined first target data. For example, if the first target data is calculated based on the distance, the second target data may be the target duration. If the first target data is calculated based on the duration, the second target data may be the target distance.

According to an embodiment, the electronic device 101 may predict the second target data based on various estimation schemes as stated above. For example, the electronic device 101 may predict a plurality of corresponding target data, based on maximum oxygen consumption (Vo2Max) estimation 1751 based on exercise data, maximum oxygen consumption estimation 1753 based on profile and test results, maximum oxygen consumption estimation 1755 based on external data (e.g., data measured and inputted by a wearable device), estimation 1757 based on Dave Cameron's model, or estimation 1759 based on Pete Riegel's model. The electronic device 101 may predict the second target data based on the predicted target data.

In an element 1760, the electronic device 101 may perform the regression analysis for the target data. According to an embodiment, the electronic device 101 may determine the second target data using linear regression model 1765.

According to an embodiment, any one or a combination of the prediction with the element 1750 and the regression with the element 1760 may determine the second target data.

In an element 1770, the electronic device 101 may generate recommendation data by combining results of weight factors, based on user profile information as aforementioned based on Equation 10.

In an element 1780, the electronic device 101 may generate final recommendation data. According to an embodiment, the electronic device 101 may provide the recommendation data based on the first target data and the second target data. According to an embodiment, the electronic device 101 may provide the recommendation data by modifying the first target data and/or the second target data based at least on additional data (e.g., warm-up and cool-down periods).

In an element 1790, the electronic device 101 may provide the recommendation data.

Figure 18:
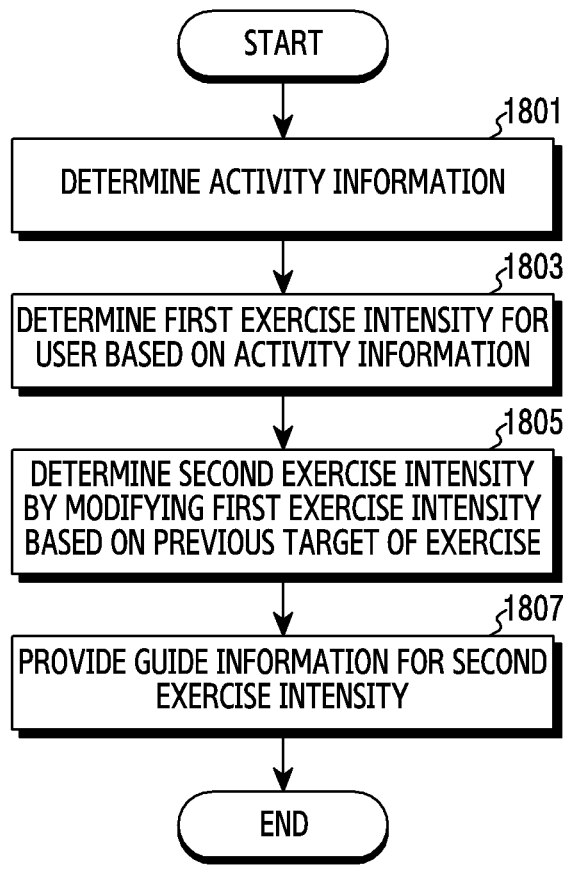
FIG. 18 is a flowchart of a method for providing a health care service in an electronic device according to various embodiments.

FIG. 18 is a flowchart of a method for providing a health care service in an electronic device according to various embodiments.

Referring to FIG. 18, in operation 1801, the processor 120 of the electronic device 101 may determine activity information. According to an embodiment, the processor 120 may determine at least one activity information which satisfies a designated condition among one or more activity information previously acquired in relation to user's activity.

According to an embodiment, the processor 120 may determine the activity information based on the workout data filtering as aforementioned. According to an embodiment, the activity information previously obtained in relation to the user's motion may include at least one of data obtained using the sensor module 176 or data stored in a server. According to an embodiment, the electronic device 101 may include communication circuitry (e.g., the communication circuit 190 of FIG. 1), and the processor 120 may receive one or more activity information (e.g., workout data stored in the server) previously obtained in relation to the user's motion, from an external electronic device (e.g., the server) connected using the communication circuitry.

In operation 1803, the processor 120 may determine a first exercise intensity (e.g., target exercise distance) for the user based on the determined activity information. According to an embodiment, based at least on variation of at least on activity information over time, the processor 120 may determine the first exercise intensity for the user. According to an embodiment, the processor 120 may determine the first exercise intensity based on the targeting operation as stated above.

According to an embodiment, the processor 120 may determine the first exercise intensity, further based on modification information with a designated weight applied to at least part of at least one activity information. In various embodiments, the modification information may include, as the smoothing result, the source distance (e.g., weighted average distance) and the source duration (e.g., weighted average duration). According to an embodiment, the modification information may include, as at least part of it, at least one of average workout distance information or average workout duration information determined based at least on at least one activity information.

In operation 1805, the processor 120 may determine a second exercise intensity by modifying the first exercise intensity based on a previous target of exercise. According to an embodiment, the processor 120 may determine the second exercise intensity by modifying the first exercise intensity based on the previous target of exercise in relation to the user. According to an embodiment, the second exercise intensity modified from the first exercise intensity may, for example, obtain and combine a target exercise duration based on a target exercise distance. According to an embodiment, if the first exercise intensity is the target exercise duration, the second exercise intensity may obtain and combine the target exercise distance based on the target exercise duration. According to an embodiment, the processor 120 may determine the second exercise intensity based on the above-stated prediction.

According to an embodiment, the processor 120 may set the target of exercise based at least on user's biometric information (e.g., profile information) of the electronic device 101. According to an embodiment, the processor 120 may include, as at least part of the first exercise intensity and the second exercise intensity, at least one of the exercise distance or the exercise duration in relation to the user's target of exercise.

According to an embodiment, the processor 120 may modify the determined second exercise intensity, based at least on designated additional information (e.g., additional data, for example, warm-up and cool-down periods). According to an embodiment, the processor 120 may combine (add) the additional information to the obtained final data.

In operation 1807, the processor 120 may provide guide information for the second exercise intensity. According to an embodiment, the processor 120 may provide the guide information based on the above-stated recommendation operation, to be explained in FIG. 19. According to an embodiment, the processor 120 may generate the guide information based at least on whether the determined second exercise intensity satisfies a designated exercise intensity range (e.g., overfitting range). According to an embodiment, the processor 120 may determine whether the second exercise intensity corresponds to the overfitting. According to an embodiment, the processor 120 may compare the second exercise intensity (e.g., the target distance and the target duration) predicted for next exercise with maximum data (e.g., maximum distance) of criteria exercise (e.g., exercise data measured by the electronic device 101 during the user's exercise, among previous exercise data of the user).

According to various embodiments, the electronic device 101 may include communication circuitry (e.g., the communication module 190 of FIG. 1), and the processor 120 may transmit data of the determined second exercise intensity to an external electronic device coupled to the electronic device 101 using the communication circuitry. According to an embodiment, data of the target of exercise (e.g., the second exercise intensity) determined at the electronic device 101 may be transmitted to the external electronic device (e.g., exercise equipment) and used to set the exercise of the exercise equipment.

Figure 19:
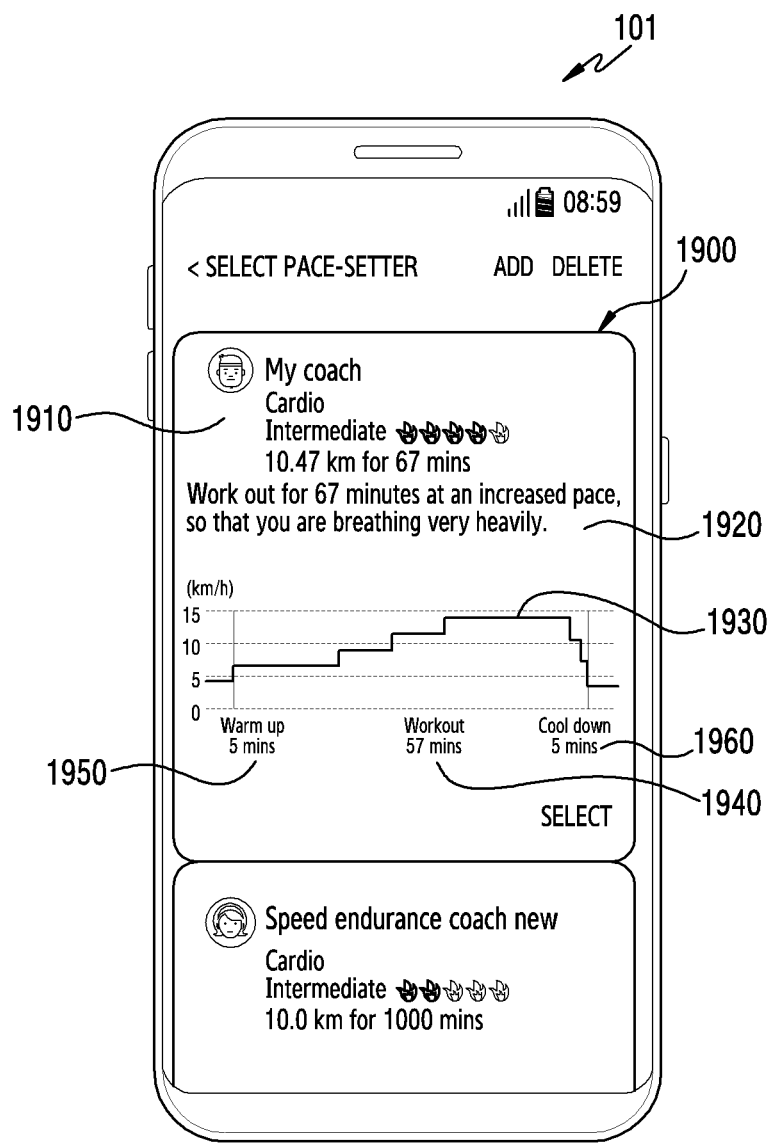
FIG. 19 is a diagram of an example of a user interface regarding exercise coach in an electronic device according to various embodiments.

FIG. 19 is a diagram of an example of a user interface regarding exercise coach in an electronic device according to various embodiments.

Referring to FIG. 19, the electronic device 101 may provide recommendation data, as one of an exercise program, to the user through the display 160 (or the display 210) based on a user interface (UI) 1900. The UI 1900 may include the exercise program based on the recommendation program, and other exercise program pre-designated.

According to an embodiment, the recommendation data 1900 may include exercise program information 1910 and exercise coach information 1920 and 1930.

The exercise program information 1910 may include an exercise program name (e.g., My coach), an exercise type (e.g., burn fat, cardio), an exercise level (e.g., a beginning level, an intermediate level, an advanced level), and exercise amount information (e.g., 10.47 km for 67 mins). The exercise program information 1910 may be provided as a combination of at least part of a text, an image (e.g., a user face image), or an icon.

The exercise coach information 1920 and 1930 may include exercise guide information 1920 and exercise period information 1930. According to an embodiment, the exercise period information 1930 may be provided based on a figure (e.g., graph) and a text. According to an embodiment, the exercise period information 1930 may be divided into graph information 1930 per exercise period, a target period 1970, a warm-up period 1950, and a cool-down period 1960.

According to an embodiment, the electronic device 101 may provide the user with audio guide according to the user's exercise status, based on the exercise coach information 1920 and 1930.

As stated above, a method for operating an electronic device 101 may include determining at least one activity information which satisfies a designated condition among one or more activity information previously obtained in relation to a user motion, determining a first exercise intensity for the user, based at least on variation of the at least one activity information over time, determining a second exercise intensity by adjusting the first exercise intensity based at least on a previous target of exercise of the user, and providing guide information associated with the second exercise intensity.

According to various embodiments, determining the first exercise intensity may include determining the first exercise intensity, further based on modification information by applying a designated weight to at least part of the at least one activity information.

According to various embodiments, as at least part of the modification information, at least one of average workout distance information or average workout duration information determined based at least on the at least one activity information may be included.

According to various embodiments, the method may further include setting the target of exercise, based at least on biometric information of the user.

According to various embodiments, the method may further include transmitting data of the determined second exercise intensity to an external electronic device which is connected, using the communication circuitry.

According to various embodiments, as at least part of the first exercise intensity and the second exercise intensity, at least one of a workout distance or a workout duration in relation to the target of exercise of the user may be included.

According to various embodiments, the method may further include receiving one or more activity information previously obtained in relation to the user motion, from an external electronic device which is connected, using the communication circuitry.

According to various embodiments, the method may further include modifying the determined second exercise intensity, based at least on designated additional information.

According to various embodiments, providing the guide information may include generating the guide information, based at least on whether the determined second exercise intensity satisfies a designated exercise intensity range.

As stated above, a method for operating an electronic device 101 according to various embodiments may include obtaining source data from exercise data of previous exercise of a user, determining first target data from at least part of the source data, estimating a plurality of prediction results for second target data, using the source data and the first target data, determining the second target data based on an average of the prediction results, and generating recommendation data for exercise coach of the user based on the first target data and the second target data.

According to various embodiments, obtaining the source data may include filtering the exercise data based on at least one condition.

According to various embodiments, obtaining the source data may include smoothing the filtered exercise data, and obtaining a source duration and a source distance from a smoothing result.

According to various embodiments, if the filtered exercise data exceeds a criteria number, the method may further include reducing by the criteria number based on recent exercise data.

According to various embodiments, determining the first target data may include presetting or determining a type of the first target data based on user preference.

According to various embodiments, estimating the prediction results may include estimating the prediction results based on a plurality of different estimation schemes.

According to various embodiments, determining the second target data may include determining the second target data based on a linear regression model using the exercise data.

According to various embodiments, generating the recommendation data may include generating the recommendation data by combining additional data with at least part of the first target data and the second target data.

According to various embodiments, generating the recommendation data may include processing the recommendation data in response to determining overfitting of the recommendation data.

According to various embodiments, the method may further include registering the recommendation data as an exercise program of the electronic device.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device comprising:
   sensor circuitry; and
   a processor,
   wherein the processor is configured to filter at least one activity information which satisfies a designated condition among one or more activity information previously obtained in relation to a user motion,
   to obtain at least one source data from the at least one activity information using exponential smoothing, wherein the exponential smoothing is a method of weighted moving average prediction schemes which assign a greatest weight to the most recent data of a time series data and exponentially decrease a weight over time,
   to determine a first exercise intensity for the user, based on the at least one source data, wherein the first exercise intensity includes exercise distance data,
   to obtain a plurality of estimated values associated with time data from the first exercise intensity based on a maximum oxygen consumption,
   to obtain an average value of the plurality of estimated values,
   to determine a second exercise intensity by adjusting the first exercise intensity, based on the average value, wherein the second exercise intensity includes exercise distance data and exercise time data,
   to modify the second exercise intensity by combining additional data in the determined second exercise intensity, and
   to provide guide information associated with a modified second exercise intensity.

2. The electronic device of claim 1, wherein the processor is configured to determine the first exercise intensity, further based on modification information by applying a designated weight to at least part of the at least one activity information.

3. The electronic device of claim 2, wherein the processor is configured to include, as at least part of the modification information, at least one of average workout distance information or average workout duration information determined based at least on the at least one activity information.

4. The electronic device of claim 1, wherein the processor is configured to set a target of exercise, based at least on biometric information of the user.

5. The electronic device of claim 1, further comprising:
   communication circuitry,
   wherein the processor is configured to transmit data of the determined second exercise intensity to an external electronic device that is connected, using the communication circuitry.

6. The electronic device of claim 1, wherein the processor is configured to include, as at least part of the first exercise intensity and the second exercise intensity, at least one of a workout distance or a workout duration in relation to a target of exercise of the user.

7. The electronic device of claim 1, further comprising:
   communication circuitry,
   wherein the processor is configured to receive one or more activity information previously obtained in relation to the user motion from an external electronic device which is connected using the communication circuitry.

8. The electronic device of claim 1, wherein the processor is configured to modify the determined second exercise intensity, based at least on designated additional information.

9. The electronic device of claim 1, wherein the processor is configured to generate the guide information, based at least on whether the determined second exercise intensity satisfies a designated exercise intensity range.

10. The electronic device of claim 1, wherein the processor is configured to determine the at least one activity information based on a criteria number.

11. A method for operating an electronic device, comprising:
    filtering at least one activity information which satisfies a designated condition among one or more activity information previously obtained in relation to a user motion;
    obtaining at least one source data from the at least one activity information using exponential smoothing, wherein the exponential smoothing is a method of weighted moving average prediction schemes which assign a greatest weight to the most recent data of a time series data and exponentially decrease a weight over time;
    determining a first exercise intensity for the user, based on the at least one source data, wherein the first exercise intensity includes exercise distance data;
    obtaining a plurality of estimated values associated with time data from the first exercise intensity based on a maximum oxygen consumption;
    obtaining an average value of the plurality of estimated values;
    determining a second exercise intensity by adjusting the first exercise intensity based on the average value, wherein the second exercise intensity includes exercise distance data and exercise time data;
    modifying the second exercise intensity by combining additional data in the determined second exercise intensity; and
    providing guide information associated with a modified second exercise intensity.

12. The method of claim 11, wherein determining the first exercise intensity comprises:
    determining the first exercise intensity, further based on modification information by applying a designated weight to at least part of the at least one activity information.

13. The method of claim 12, wherein, as at least part of the modification information, at least one of average workout distance information or average workout duration information determined based at least on the at least one activity information is included.

14. The method of claim 11, further comprising:
setting a target of exercise, based at least on biometric information of the user.

15. The method of claim 11, further comprising:
transmitting data of the determined second exercise intensity to an external electronic device which is connected using communication circuitry.

* * * * *